(12) United States Patent
Wang et al.

(10) Patent No.: US 8,777,832 B1
(45) Date of Patent: Jul. 15, 2014

(54) AXIAL-CENTRIFUGAL FLOW CATHETER PUMP FOR CAVOPULMONARY ASSISTANCE

(71) Applicant: The University of Kentucky Research Foundation, Lexington, KY (US)

(72) Inventors: Dongfang Wang, Lexington, KY (US); Joseph B. Zwischenberger, Lexington, KY (US)

(73) Assignee: The University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 13/803,939

(22) Filed: Mar. 14, 2013

(51) Int. Cl.
*A61M 1/12* (2006.01)
*A61M 1/10* (2006.01)

(52) U.S. Cl.
CPC .................................. *A61M 1/1012* (2014.02)
USPC ............................................................. 600/16

(58) Field of Classification Search
USPC .................................................... 623/3.1–3.3
See application file for complete search history.

(56) References Cited

U.S. PATENT DOCUMENTS

| | | | |
|---|---|---|---|
| 973,868 A | 10/1910 | Kneuper |
| 2,273,558 A | 2/1942 | Burgess |
| 2,474,665 A | 6/1949 | Guarino |
| 2,742,158 A | 4/1956 | Schuller |
| 3,103,928 A | 9/1963 | Broman |
| 3,183,908 A | 5/1965 | Collins et al. |
| 3,410,263 A | 11/1968 | McGinnis |
| 3,429,443 A | 2/1969 | Howard |
| 3,768,977 A | 10/1973 | Brumfield et al. |
| 3,855,995 A | 12/1974 | Bentley |
| 3,856,475 A | 12/1974 | Marx |
| 3,898,045 A | 8/1975 | Bowley |
| 3,934,982 A | 1/1976 | Arp |
| 3,935,110 A | 1/1976 | Schmid et al. |
| 3,960,657 A | 6/1976 | Bowley |
| 4,017,279 A | 4/1977 | Bowley |
| 4,094,792 A | 6/1978 | Bentley |
| 4,098,275 A | 7/1978 | Consalvo |
| 4,134,402 A | 1/1979 | Mahurkar |
| 4,188,360 A | 2/1980 | Kurata |
| 4,196,075 A | 4/1980 | Bentley |
| 4,205,042 A | 5/1980 | Giurtino et al. |
| 4,268,476 A | 5/1981 | Raible |
| 4,297,318 A | 10/1981 | Raible |
| 4,368,118 A | 1/1983 | Siposs |
| 4,372,914 A | 2/1983 | Raible |
| 4,374,088 A | 2/1983 | Stenberg et al. |
| 4,533,516 A | 8/1985 | Johnsson et al. |
| 4,568,253 A | 2/1986 | Wood |
| 4,573,883 A | 3/1986 | Noon et al. |
| 4,612,126 A | 9/1986 | Alt et al. |
| 4,623,518 A | 11/1986 | Raible |
| 4,698,207 A | 10/1987 | Bringham et al. |
| 4,770,652 A | 9/1988 | Mahurkar |
| 4,808,155 A | 2/1989 | Mahurkar |

(Continued)

*Primary Examiner* — Paula J Stice
(74) *Attorney, Agent, or Firm* — King & Schickli, PLLC

(57) ABSTRACT

An axial-centrifugal flow catheter pump for cavopulmonary assistance is provided, incorporating a rotor providing both an axial fluid flow and a centrifugal fluid flow. The rotor includes a first terminal impeller configured to provide a centrifugal and axial fluid flow in a first direction, a second terminal impeller configured to provide a centrifugal and axial fluid flow in a second direction opposite to the first direction, and a central impeller configured to provide a predominantly centrifugal fluid flow. The first and second terminal impellers each include blade arrangements configured to provide a centrifugal and axial fluid flow directed toward the rotor central impeller. Cavopulmonary assistance devices are provided including the axial-centrifugal flow catheter pump.

20 Claims, 8 Drawing Sheets

(56) References Cited

U.S. PATENT DOCUMENTS

| | | |
|---|---|---|
| 4,846,152 A | 7/1989 | Wampler et al. |
| 4,874,581 A | 10/1989 | Sutherland et al. |
| 4,906,229 A | 3/1990 | Wampler |
| 4,908,014 A | 3/1990 | Kroyer |
| 4,915,837 A | 4/1990 | Verity |
| 4,925,377 A | 5/1990 | Inacio et al. |
| 4,975,247 A | 12/1990 | Badolato et al. |
| 5,034,188 A | 7/1991 | Nakanishi et al. |
| RE33,932 E | 5/1992 | Fukasawa et al. |
| 5,116,308 A | 5/1992 | Hagiwara |
| 5,120,501 A | 6/1992 | Mathewson et al. |
| 5,139,741 A | 8/1992 | Hagiwara |
| 5,158,533 A | 10/1992 | Strauss et al. |
| 5,188,732 A | 2/1993 | De Niel et al. |
| 5,197,951 A | 3/1993 | Mahurkar |
| 5,217,689 A | 6/1993 | Raible |
| 5,221,255 A | 6/1993 | Mahurkar et al. |
| 5,225,161 A | 7/1993 | Mathewson et al. |
| 5,236,665 A | 8/1993 | Mathewson et al. |
| 5,270,004 A | 12/1993 | Cosentino et al. |
| 5,270,005 A | 12/1993 | Raible |
| 5,282,783 A | 2/1994 | Lindsay |
| 5,316,724 A | 5/1994 | Mathewson et al. |
| 5,338,512 A | 8/1994 | Mathewson et al. |
| 5,354,277 A | 10/1994 | Guzman et al. |
| 5,358,689 A | 10/1994 | Jones et al. |
| 5,374,245 A | 12/1994 | Mahurkar |
| 5,395,525 A | 3/1995 | Takano et al. |
| 5,421,405 A | 6/1995 | Goodin et al. |
| 5,476,444 A | 12/1995 | Keeling et al. |
| 5,507,629 A | 4/1996 | Jarvik |
| 5,578,077 A | 11/1996 | Kassatly |
| 5,718,871 A | 2/1998 | Elgas |
| 5,725,357 A | 3/1998 | Nakazeki et al. |
| 5,762,868 A | 6/1998 | Leonard |
| 5,762,875 A | 6/1998 | Gremel et al. |
| 5,770,149 A | 6/1998 | Raible |
| 5,787,729 A | 8/1998 | Wijaya |
| 5,788,287 A | 8/1998 | Gremel |
| 5,817,279 A | 10/1998 | Eilers et al. |
| 5,823,987 A | 10/1998 | Elgas et al. |
| 5,851,174 A | 12/1998 | Jarvik et al. |
| 5,858,233 A | 1/1999 | Elgas et al. |
| 5,906,741 A | 5/1999 | Elgas et al. |
| 5,922,202 A | 7/1999 | Elgas et al. |
| 5,958,255 A | 9/1999 | Hobrecht et al. |
| 5,964,694 A | 10/1999 | Siess et al. |
| 6,017,493 A | 1/2000 | Cambron et al. |
| 6,048,363 A | 4/2000 | Nagyszalanczy et al. |
| 6,220,832 B1 | 4/2001 | Schob |
| 6,224,829 B1 | 5/2001 | Piplani et al. |
| 6,247,892 B1 | 6/2001 | Kazatchkov et al. |
| 6,336,911 B1 | 1/2002 | Westerbeck |
| 6,368,557 B1 | 4/2002 | Piplani et al. |
| 6,379,618 B1 | 4/2002 | Piplani et al. |
| 6,395,226 B1 | 5/2002 | Plunkett |
| 6,406,452 B1 | 6/2002 | Westerbeck |
| 6,413,233 B1 | 7/2002 | Sites et al. |
| 6,428,747 B1 | 8/2002 | Dueri et al. |
| 6,454,999 B1 | 9/2002 | Farhangnia et al. |
| 6,497,841 B1 | 12/2002 | Plotkin et al. |
| 6,503,450 B1 | 1/2003 | Afzal et al. |
| 6,508,983 B1 | 1/2003 | McBurney et al. |
| 6,527,699 B1 | 3/2003 | Goldowsky |
| 6,572,821 B2 | 6/2003 | Knott |
| 6,579,496 B1 | 6/2003 | Fausset et al. |
| 6,613,008 B2 | 9/2003 | Aboul-Hosn et al. |
| 6,630,107 B1 | 10/2003 | Merce Vives |
| 6,644,320 B2 | 11/2003 | Groth et al. |
| 6,669,661 B1 | 12/2003 | Yee |
| 6,682,698 B2 | 1/2004 | Chambers et al. |
| 6,689,315 B2 | 2/2004 | Linker et al. |
| 6,716,157 B2 | 4/2004 | Goldowsky |
| 6,716,188 B2 | 4/2004 | Noda et al. |
| 6,723,283 B2 | 4/2004 | Ghelli et al. |
| 6,726,653 B2 | 4/2004 | Noda et al. |
| 6,730,267 B2 | 5/2004 | Stringer et al. |
| 6,746,416 B2 | 6/2004 | Hubbard et al. |
| 6,884,360 B2 | 4/2005 | Chang |
| 6,908,446 B2 | 6/2005 | Yokoyama et al. |
| 6,960,322 B2 | 11/2005 | Stringer et al. |
| 7,022,099 B2 | 4/2006 | Litzie et al. |
| 7,022,284 B2 | 4/2006 | Brian et al. |
| 7,135,008 B2 | 11/2006 | O'Mahony et al. |
| 7,238,320 B2 | 7/2007 | Ghelli et al. |
| 7,541,000 B2 | 6/2009 | Stringer et al. |
| 7,704,054 B2 | 4/2010 | Horvath et al. |
| 7,785,247 B2 | 8/2010 | Tatum et al. |
| 8,152,443 B1 | 4/2012 | Pemberton |
| 2004/0226868 A1 | 11/2004 | Shoji et al. |
| 2006/0009728 A1 | 1/2006 | Litzie et al. |
| 2006/0177343 A1 | 8/2006 | Brian, III et al. |
| 2006/0253194 A1 | 11/2006 | Dial |
| 2007/0073393 A1 | 3/2007 | Kung et al. |
| 2007/0217948 A1 | 9/2007 | Ghelli et al. |
| 2007/0249888 A1 | 10/2007 | Wu et al. |
| 2008/0199357 A1 | 8/2008 | Gellman et al. |
| 2008/0234623 A1 | 9/2008 | Strauss et al. |
| 2010/0168848 A1 | 7/2010 | Horvath et al. |
| 2011/0257462 A1 | 10/2011 | Rodefeld et al. |
| 2012/0095280 A1 | 4/2012 | Timms |
| 2013/0094997 A1 | 4/2013 | Wang et al. |

AXIAL-CENTRIFUGAL FLOW CATHETER PUMP FOR CAVOPULMONARY ASSISTANCE

TECHNICAL FIELD

The present invention relates generally to the field of medical devices. In particular, the invention relates to cardiac medical devices and systems for use in remediating or alleviating failing circulation subsequent to a Fontan procedure.

BACKGROUND OF THE INVENTION

The Fontan or Fontan/Kreutzer procedure is a palliative (not curative) surgical procedure used to ameliorate complex congenital heart defects, especially in the young. Exemplary heart defects addressed by the Fontan procedure include heart valve defects (tricuspid atresia, pulmonary atresia), abnormalities in pumping ability of the heart (hypoplastic left heart syndrome, hypoplastic right heart syndrome), and other complex congenital heart diseases where a bi-ventricular repair is not possible or contra-indicated (double inlet left ventricle, hetertaxy defects, double outlet right ventricle, etc.). The process was initially described as a surgical treatment for tricuspid atresia.

As a result of the Fontan procedure, a surgically created junction is provided between the superior and inferior vena cava and the pulmonary artery, and venous blood flow is diverted from the superior and inferior vena cava directly to the pulmonary artery, bypassing the right ventricle of the heart. Following the procedure, oxygen-poor blood from the upper and lower body flows through the lungs without being pumped by the heart. Rather, the blood flow into the lungs is driven only by central venous blood pressure. This corrects hypoxia, and leaves a single heart ventricle responsible only for supplying blood to the body.

However, disadvantages and post-surgical complications are associated with the Fontan procedure. In the short term, pleural effusions (fluid build-up around the lungs) can occur, requiring additional surgical interventions. In the long term, atrial scarring may be associated with atrial flutter and atrial fibrillation, also requiring additional surgical intervention. Other long-term risks may be associated with the procedure, such as protein-losing enteropathy and chronic renal insufficiency, although these latter risks are not yet fully quantified.

Also, a high central venous pressure is required to provide a satisfactory supply of blood to the lungs after the Fontan procedure. Immediately or even 2-5 years following the procedure, it is known that the surgically created Fontan circulation often fails due to that high venous pressure required to drive pulmonary circulation. Long term mortality following the Fontan procedure can be as high as 29.1%, characterized by catastrophic failure of circulation and death. The expected event-free survival rate following the Fontan procedure at one, ten, and twenty-five years following the procedure is 80.1%, 74.8%, and 53.6%, respectively. A bi-modal age distribution has been observed in failing Fontan circulation. In early post-operative cases of failing Fontan circulation, the Fontan connection must be surgically taken down. In later post-operative cases, often the only remedy is heart transplantation.

Because of the above complications, in cases of failing Fontan circulation cavopulmonary assistance is often indicated, to actively move blood from the superior/inferior vena cava into pulmonary circulation, to decrease the central venous pressure required to provide the needed flow of blood to the lungs, and to reverse the pathophysiology associated with failing Fontan circulation. Attempts have been made to alleviate failing Fontan circulation by implanting a right ventricular assist device (RVAD). However, this requires a traumatic surgical intervention to implate the device, and also requires take-down of the Fontan connection to allow pump installation. Dual hemopumps have been evaluated to restore or assist failing Fontan circulation. However, in such cases using two hemopumps, two surgical site cannulations are required, which is unduly traumatic to a patient. Also, patient mobility is severely restricted when two pumps must be deployed by cannulation.

A number of smaller pumps have been evaluated, but most require two pumping mechanisms for deployment in the superior and inferior vena cava (above and below the surgically created Fontan connection) to move blood toward and into pulmonary circulation. Because of the dual pumps/dual cannulations required, such pumps cannot be made ambulatory, i.e. the patient must be substantially bedridden after deployment of the pumps. Single pump mechanisms have been evaluated. Such pumps can create the required flow of blood into the pulmonary artery, but are difficult to deploy and consistently maintain in position due to the need for precise placement at the Fontan anastomosis surgically created at the juncture of the superior/inferior vena cava and the pulmonary artery. Proper alignment of this type of pump at the pulmonary artery and retaining that proper alignment is difficult to impossible, even with patient sedation, and further because of the difficulting in maintaining proper positioning after deployment, such pumps cannot be made ambulatory. Still other single pump mechanisms considered require surgical creation of an offset between the superior and inferior vena cava to promote blood flow into the pulmonary artery, increasing surgical difficulty and resultant complications for the patient.

There is accordingly a need in the art for improvements to pumps for cavopulmonary assistance in the event of failing Fontan circulation. Such improved pumps should require only a single pump mechanism requiring only one cannulation, but should still create satisfactory blood flow from both the superior and inferior vena cava into the pulmonary artery. Moreover, the pump should be relatively simple to deploy at the surgically created Fontan connection site, should not require absolutely precise placement to provide proper pump operation and blood flow, and should allow for a degree of displacement after deployment without affecting proper pump operation and blood flow. Still more, the pump should be ambulatory, allowing patient mobility and improved comfort after the procedure.

SUMMARY OF THE INVENTION

In accordance with the above-identified need in the art, in one aspect the present disclosure provides an axial-centrifugal flow catheter pump for cavopulmonary assistance, including a rotor having elements providing both an axial fluid flow and a centrifugal fluid flow and a motor operatively connected to the rotor. The rotor includes a first terminal impeller configured to provide a centrifugal and axial fluid flow in a first direction, a second terminal impeller configured to provide a centrifugal and axial fluid flow in a second direction opposite to the first direction, and a central impeller configured to provide a predominantly centrifugal fluid flow. To provide the desired fluid flow patterns, the first and second terminal impellers each include blade arrangements configured to provide a centrifugal and axial fluid flow directed toward the rotor central impeller. The first and second terminal impeller blade arrangements may transition over the longitudinal axis of the rotor to define the central impeller blade arrangement, or alternatively the first and second terminal impeller blade arrangements and the central blade arrangement may be separate.

In another aspect, a rotor as described above is provided for a two-stage axial-centrifugal flow catheter pump for cavopulmonary assistance.

In yet another aspect, a cavopulmonary assistance device is provided including an axial axial-centrifugal flow catheter pump as described above. The device includes a motor operatively connected to the rotor, a cable connected to the rotor and/or the motor, and a deployable anchor for securing the cavopulmonary assistance device to a blood vessel wall. The motor may be directly connected to the rotor, or may be remotely operatively connected to the rotor such as via the cable. The deployable anchor is configured to allow fluid flow therethrough when deployed. A protective enclosure allowing fluid flow therethrough surrounds at least the rotor to prevent damage to a blood vessel wall.

These and other embodiments, aspects, advantages, and features of the present invention will be set forth in the description which follows, and in part will become apparent to those of ordinary skill in the art by reference to the following description of the invention and referenced drawings or by practice of the invention. The aspects, advantages, and features of the invention are realized and attained by means of the instrumentalities, procedures, and combinations particularly pointed out in the appended claims. Various patent and non-patent citations are discussed herein. Unless otherwise indicated, any such citations are specifically incorporated by reference in their entirety into the present disclosure.

BRIEF DESCRIPTION OF THE DRAWINGS

The accompanying drawings incorporated in and forming a part of the specification, illustrate several aspects of the present invention, and together with the description serve to explain the principles of the invention. In the drawings.

DETAILED DESCRIPTION OF THE ILLUSTRATED EMBODIMENTS

In the following detailed description of the illustrated embodiments, reference is made to the accompanying drawings that form a part hereof, and in which is shown by way of illustration, specific embodiments in which the invention may be practiced. These embodiments are described in sufficient detail to enable those skilled in the art to practice the invention. Also, it is to be understood that other embodiments may be utilized and that process, reagent, software, and/or other changes may be made without departing from the scope of the present invention.

Figure 1:
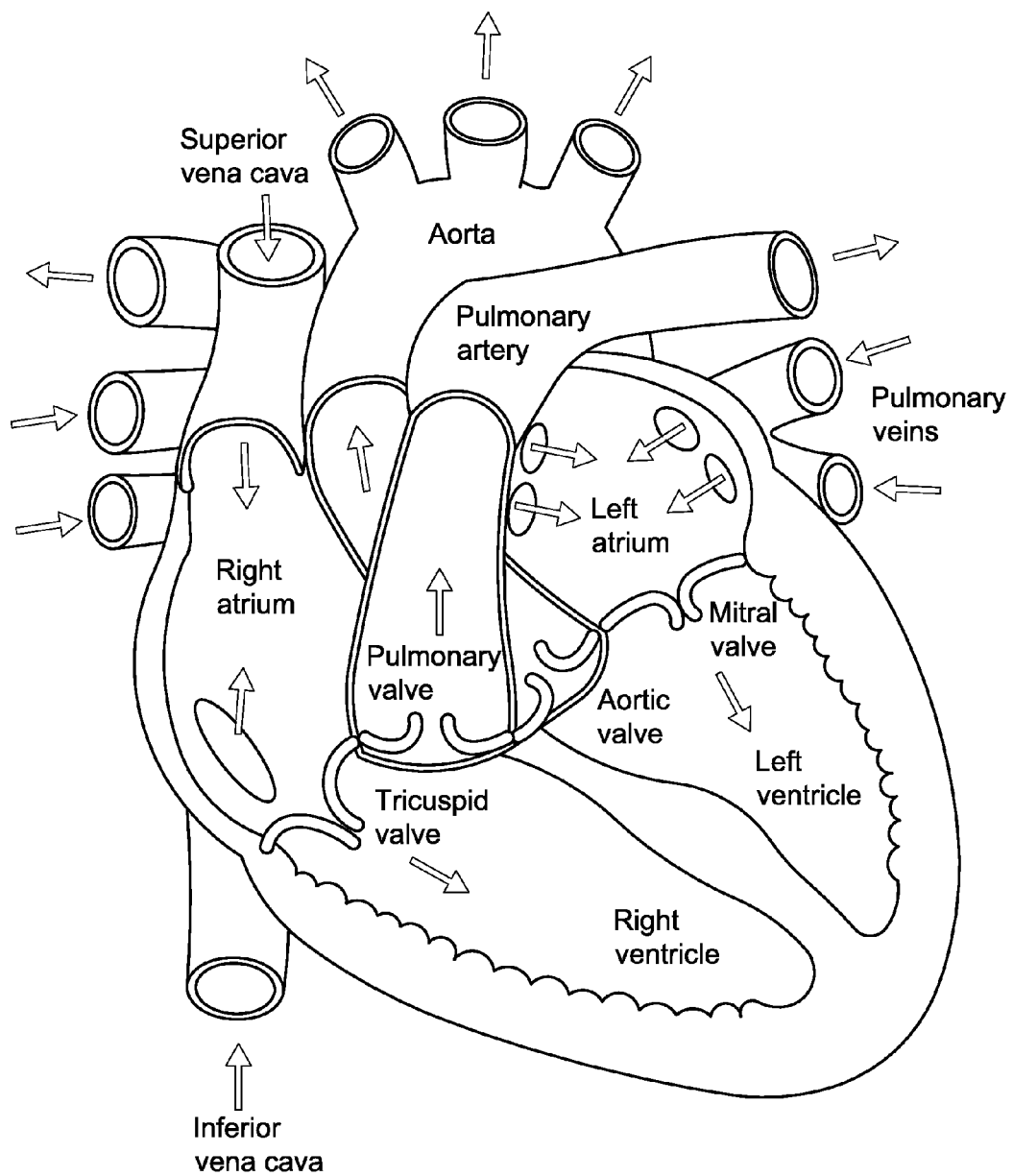
FIG. 1 depicts a normal human heart.
Figure 2:
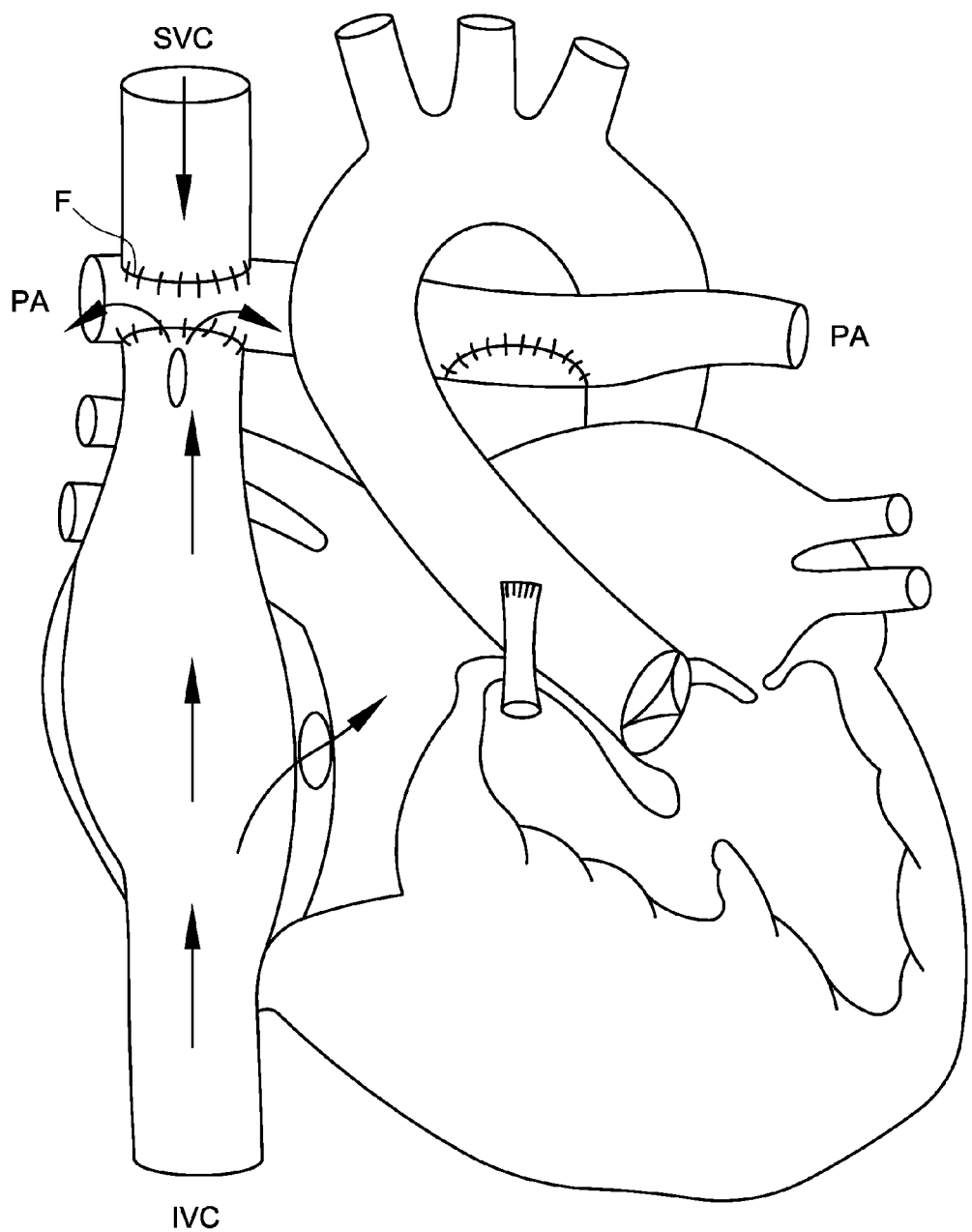
FIG. 2 depicts the heart of FIG. 1 after completion of a Fontan procedure, showing the Fontan anastomosis placing the superior and inferior vena cava in fluid communication with the pulmonary artery.

In the normal heart (see FIG. 1), there is no direct fluid communication between the superior vena cava (SVC), inferior vena cava (IVC), and the pulmonary artery (PA). As is known in the art and as summarized above, in the Fontan procedure venous blood flow is diverted from the SVC and IVC directly to the PA, bypassing the right ventricle of the heart. By the procedure, a surgically created junction (Fontan anastomosis F) is provided between the superior and inferior vena cava and the pulmonary artery to allow fluid communication between the vessels and directly into pulmonary circulation (see FIG. 2). As summarized above, this Fontan circulation is prone to failure, requiring additional intervention to reverse or ameliorate failing Fontan circulation and associated pathologies.

In one aspect, the present disclosure provides a rotor 10 (see FIG. 3) for an axial-centrifugal flow pump. The rotor 10 includes first and second terminal impellers 12, 14 and an elongated central shaft 16 supporting a central impeller 18. The first and second impellers 12, 14 are each configured to create a centrifugal and axial fluid flow when rotor 10 is rotated, specifically wherein the first and second impellers 12, 14 create axial fluid flows in opposed directions (see arrows A). In particular embodiments, the first and second impellers 12, 14 include at least one blade 20 disposed at an included angle of from about 10 to about 30 degrees relative to a longitudinal axis of the rotor 10 to provide the desired axial and centrifugal fluid flow.

The central impeller 18, on the other hand, includes at least one blade 22 disposed whereby rotation of rotor 10 creates a predominantly centrifugal fluid flow around central impeller 16 (see arrows B). In particular embodiments, the central impeller 18 includes at least one blade 22 disposed at an included angle of from about 80 to about 100 degrees relative to a longitudinal axis of the rotor 10 to provide the desired centrifugal fluid flow. In use, rotation of the rotor 10 will cause first and second impellers 12, 14 to promote a centrifugal and axial flow of fluid in the direction of central impeller 18, while central impeller 18 redirects that axial fluid flow into a primarily centrifugal fluid flow.

Figure 3:
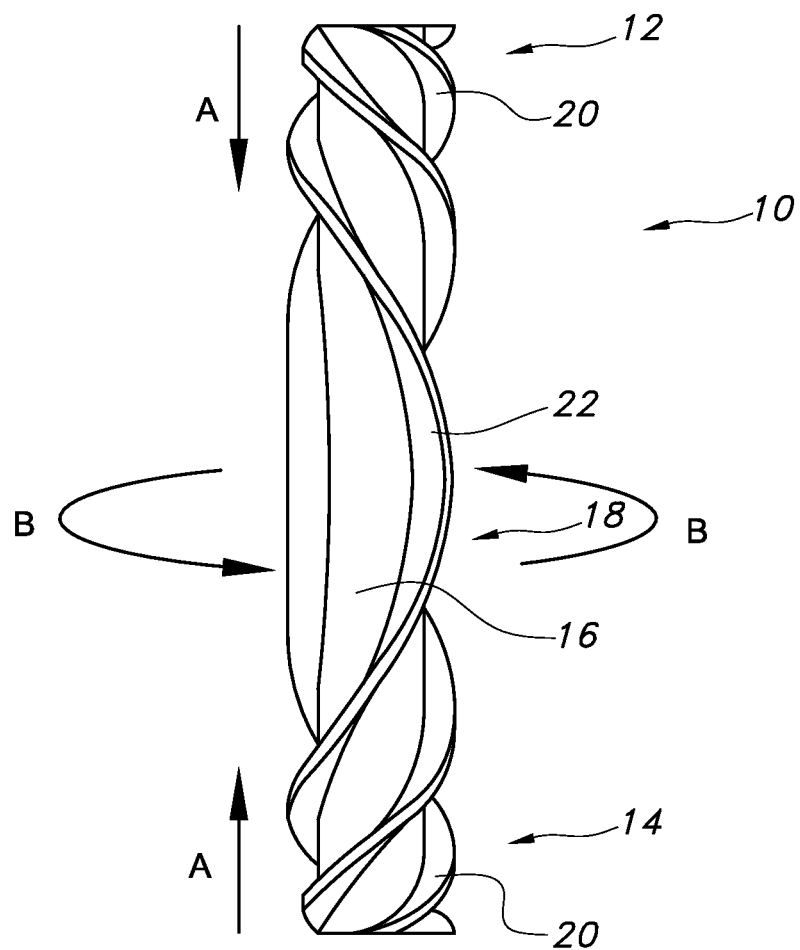
FIG. 3 depicts an embodiment of a rotor for an axial-centrifugal flow pump.
Figure 4A:
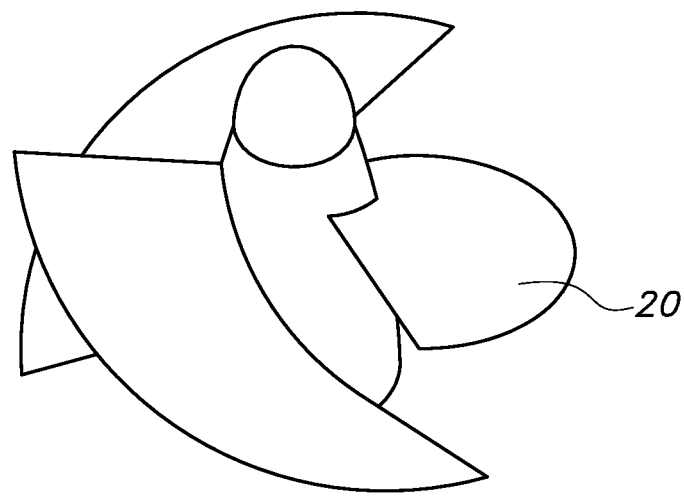
FIGS. 4a, 4b, and 4c depict alternative embodiments of blade configurations for the impellers of the rotor of FIG. 3.
Figure 4B:
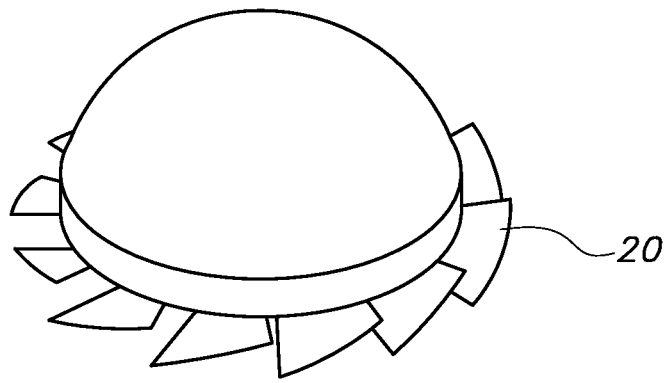
Figure 4C:
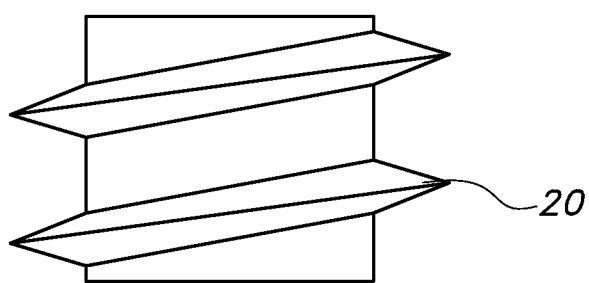

In the embodiment shown in FIG. 3, the blades 20, 22 are of the Archimedean screw type. In the depicted embodiment of FIG. 3, blades 20 of the first and second impellers 12, 14 transition over a longitudinal axis of the rotor 10 to define the blades 22 of the central impeller 18. However, a variety of blade configurations are contemplated for inclusion in the rotor 10 described above. As a non-limiting example, a propeller or screw type blade 20 is contemplated for use in first and second impellers 12, 14 (see FIG. 4a). Alternatively, first and second impellers 12, 14 may include a plurality of discrete blades 20 (see FIG. 4b); with the caveat that the blades 20 must be oriented such that a centrifugal and axial fluid flow is promoted as described above. As another alternative, an auger-type blade 20 may be used (see FIG. 4c). Similar arrangements are contemplated for use as blades 22 of central impeller 18, with the caveat that the blades 22 must be oriented such that a predominantly centrifugal fluid flow is promoted by the central impeller 18 as described above.

Figure 5A:
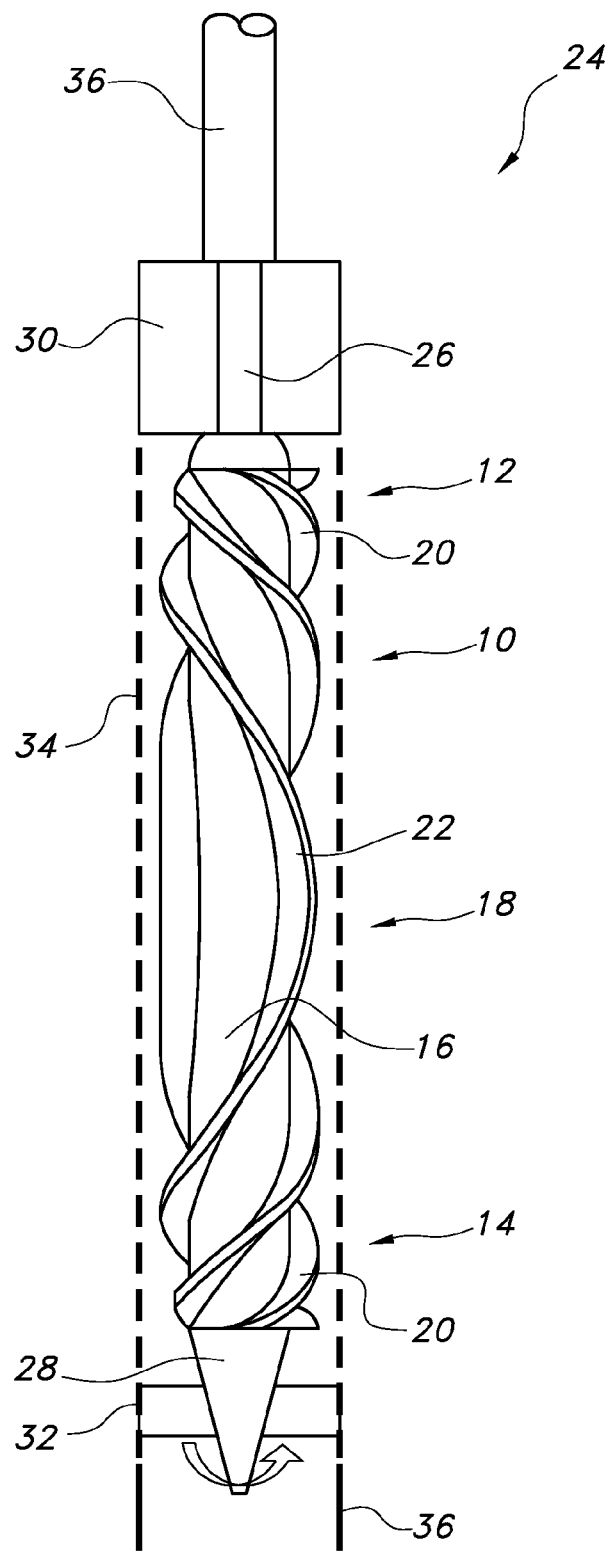
FIGS. 5a and 5b depict embodiments of axial-centrifugal flow pumps according to the present disclosure.

In another aspect (see FIG. 5a), the present disclosure provides an axial-centrifugal flow pump 24 incorporating the rotor 10 as described above, for use as a cavopulmonary assistance device (CPAD). The rotor 10 is provided with bearing arrangements 26, 28 at opposed ends thereof to allow rotation of rotor 10. A number of bearings are contemplated for use as bearings 26, 28, including without intending any limitation ball bearings, roller bearings, cone bearings, ball thrust bearings, roller thrust bearings, magnetic bearings, and the like.

A motor 30 is operatively connected to rotor 10 to drive rotation thereof. In the embodiment of FIG. 5, the rotor 10 is held by bearings 26 in a micro motor 30. A stator 32 is provided at the opposed end of rotor 10, to support rotation of rotor 10 in conjunction with bearing 28. In an embodiment, bearing 28 may be a cone bearing of substantially known design, supported by stator 32. However, other designs are contemplated for bearings 26, 28 as described above. A protective enclosure 34 is also provided, to prevent contact of the rotor 10 with, e.g., a blood vessel wall interior. A number of suitable enclosures 34 are contemplated, such as a cage made of wire or other suitable materials allowing blood flow therethrough to prevent fluid flow occlusion or reduction and areas of stagnant blood flow. Such devices are known in the art. An expandable or deployable anchor 36 is included at a terminus of the pump 24, whose function will be described in detail below. A cable 36 is provided at a terminus of the pump 24, one function of which is to facilitate placement of the pump 34 at a desired location in a blood vessel. In combination, cable 36 and pump 24 define a catheter pump which provides both an axial and a centrifugal fluid flow as described above, in a compact, self-contained design promoting patient mobility after placement of the pump 24.

Figure 5B:
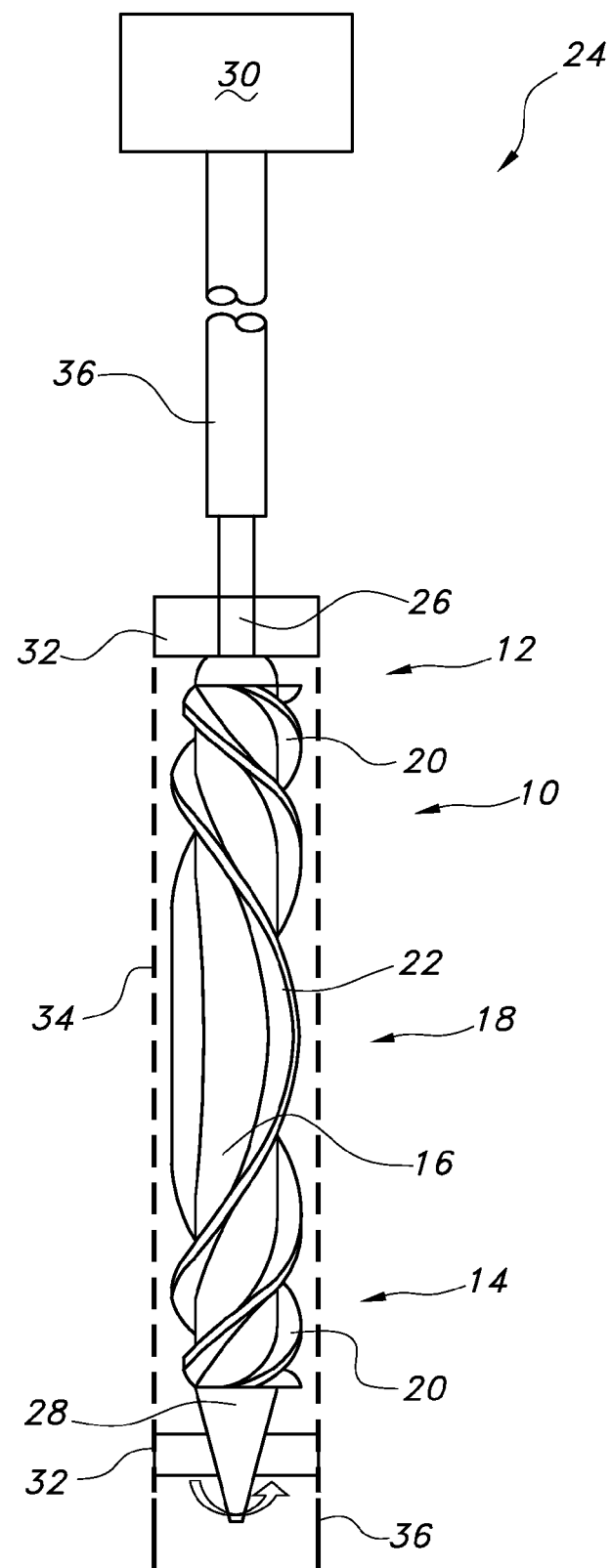

The skilled artisan will appreciate that alternative configurations are possible and are contemplated herein. For example, rather than directly associating the motor 30 with the pump 24 as depicted in the embodiment of FIG. 5, the motor 30 may be disposed remotely from the pump 24, and operatively connected to the rotor 10 via cable 36 (see FIG. 5b). A second stator 32 and bearing 26 arrangement may be included to stabilize the end of rotor 10 connected to cable 36. In this embodiment, motor 30 may be positioned extracorporeally during use of pump 24, facilitating maintenance and/or replacement thereof in case of failure.

Deployment and use of pump 24 such as in the event of failing Fontan circulation will now be described. As summarized above, the Fontan procedure results in a surgically created junction (Fontan anastomosis) between the superior and inferior vena cava and the pulmonary artery to allow fluid communication between the vessels (see FIG. 2). To improve that failing Fontan circulation, pump 24 is inserted into, for example, the right jugular vein and therefrom into the superior vena cava and advanced using cable 36 and/or a suitable guidewire/deployment catheter or balloon dilation catheter arrangement (not shown) of known design. Advancement and proper placement of pump 24 may be monitored by any suitable imaging technology, such as X-ray fluoroscopy, radiography, intravascular ultrasound, etc., to ensure proper positioning of the pump 24.

Figure 6A:
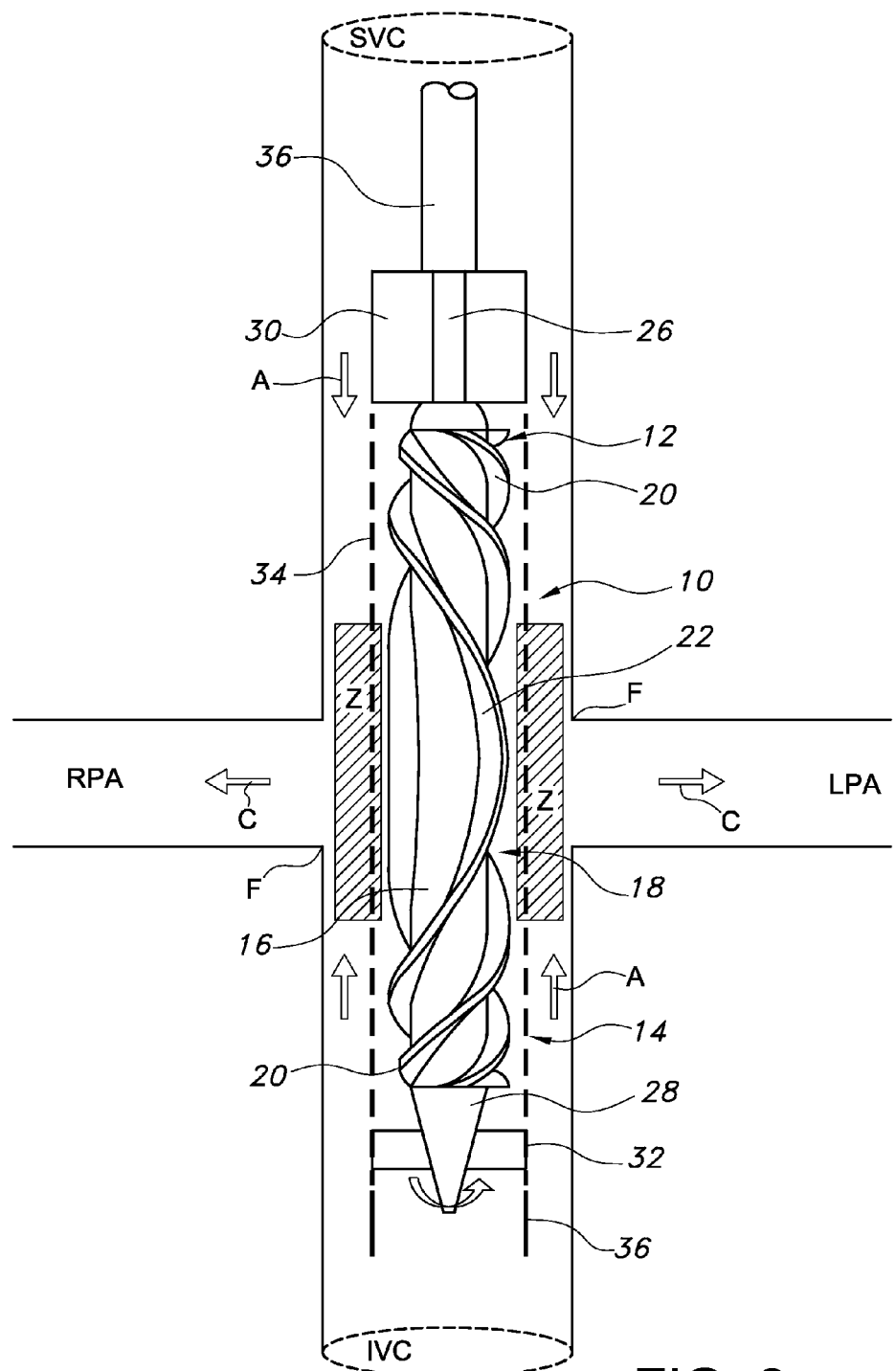
FIGS. 6a and 6b depict placement of the axial-centrifugal flow pump of FIG. 5 at a site of a Fontan anastomosis, with FIG. 6a showing the device with an undeployed anchor and FIG. 6b showing the device with a deployed anchor to secure the device to the wall of the inferior vena cava.
Figure 6B:
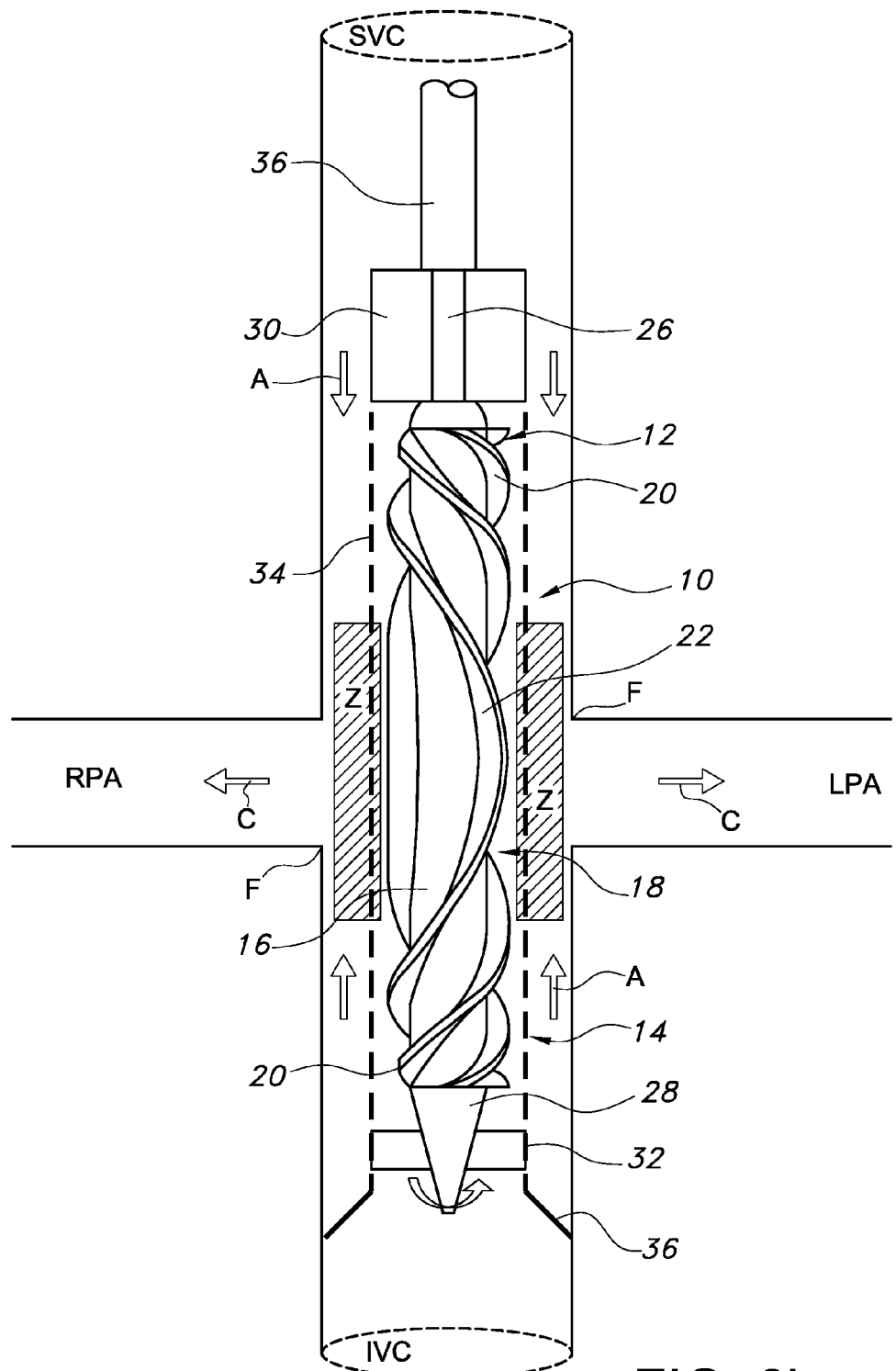

The pump 24 is advanced until the rotor 10 bridges the Fontan anastomosis F (see FIG. 6a). As shown, first impeller 12 is positioned substantially in the superior vena cava (SVC), second impeller 14 is positioned substantially in the inferior vena cava (IVC), and central impeller 18 bridges the Fontan anastomosis F, i.e. the surgically created juncture between the SVC, IVC, right pulmonary artery (RPA), and left pulmonary artery (LPA). Once proper placement of the pump 24 is verified, the expandable or deployable anchor 36 is deployed to anchor the pump 24 to the IVC vessel wall and prevent undesired movement of the pump 24 (see FIG. 6b). Typically, an anchor 36 is used which allows fluid flow therethrough after deployment, to prevent occlusion or reduction of blood flow through the blood vessel and to prevent areas of stagnant blood flow after the anchor 36 is deployed.

On rotation of rotor 10, as described above first and second impellers 12, 14 created a centrifugal and axial fluid flow of blood in the direction of central impeller 18 (see arrows A). In turn, as rotor 10 rotates, central impeller 18 creates a predominantly centrifugal fluid flow of blood substantially at the location of the Fontan anastomosis, accelerating blood spinning in this region of the superior and inferior vena cava and creating a high pressure zone in the region of the blood vessel extending between the first and second impellers 12, 14 (see shaded area Z). This provides a delivery of blood at substantially right angles into the RPA and LPA (arrows C). By the pump 24 of the present disclosure, blood flow is promoted from the superior vena cava/inferior vena cava into the pulmonary circulation, eliminating the increased central venous pressure required to promote this type of blood flow as is typically associated with Fontan procedure.

A number of advantages are realized by the rotor 10/axial-centrifugal flow pump 24 design of the present disclosure. For example, separation of the first and second impellers 12, 14 by elongated shaft 16 allows for some movement of the rotor 10/pump 24 within the superior vena cava and inferior vena cava after placement and deployment of anchor 36 without affecting the performance of pump 24 and without disrupting the blood flow created by pump 24 as described above. This eliminates the need for unduly precise placement at the site of a Fontan anastomosis associated with prior art pumps to promote the desired blood flow into pulmonary circulation, and also obviates the loss of performance of such prior art pumps if the pump is at all displaced during use. In turn, a compact, effective, and efficient pump 24 design is provided which, by its size and flexibility in placement, allows patient ambulation after the pump 24 is placed.

One of ordinary skill in the art will recognize that additional embodiments of the invention are also possible without departing from the teachings herein. This detailed description, and particularly the specific details of the exemplary embodiments, is given primarily for clarity of understanding, and no unnecessary limitations are to be imported, for modifications will become obvious to those skilled in the art upon reading this disclosure and may be made without departing from the spirit or scope of the invention. Relatively apparent modifications, of course, include combining the various features of one or more figures or examples with the features of one or more of other figures or examples.

What is claimed is:

1. An axial-centrifugal flow catheter pump for cavopulmonary assistance, comprising:
   a rotor providing both an axial fluid flow and a centrifugal fluid flow; and
   a motor operatively connected to the rotor;
   the rotor including a first terminal impeller configured to provide a centrifugal and axial fluid flow in a first direction, a second terminal impeller configured to provide a centrifugal and axial fluid flow in a second direction opposite to the first direction, and a central impeller configured to provide a predominantly centrifugal fluid flow.

2. The axial-centrifugal flow catheter pump of claim 1, wherein the first and second terminal impellers each include blade arrangements configured to provide a centrifugal and axial fluid flow directed toward the rotor central impeller.

3. The axial-centrifugal flow catheter pump of claim 2, wherein the first and second terminal impeller blade arrangements include at least one blade oriented at an included angle of from 10 to 30 degrees relative to a longitudinal axis of the rotor.

4. The axial-centrifugal flow catheter pump of claim 1, wherein the central impeller includes a blade arrangement having at least one blade oriented at an included angle of from 80 to 100 degrees relative to a longitudinal axis of the rotor.

5. The axial-centrifugal flow catheter pump of claim 4, wherein the first and second terminal impeller blade arrangements transition over the longitudinal axis of the rotor to define the central impeller blade arrangement.

6. A rotor for a two-stage axial-centrifugal flow catheter pump for cavopulmonary assistance, comprising:
a first terminal impeller configured to provide a centrifugal and axial fluid flow in a first direction;
a second terminal impeller configured to provide a centrifugal and axial fluid flow in a second direction opposite to the first direction; and
a central impeller configured to provide a predominantly centrifugal fluid flow.

7. The rotor of claim 6, wherein the first and second terminal impellers each include blade arrangements configured to provide a centrifugal and axial fluid flow directed toward the rotor central impeller.

8. The rotor of claim 7, wherein the first and second terminal impeller blade arrangements include at least one blade oriented at an included angle of from 10 to 30 degrees relative to a longitudinal axis of the rotor.

9. The rotor of claim 6, wherein the central impeller includes a blade arrangement configured to provide a predominantly centrifugal fluid flow and having at least one blade oriented at an included angle of from 80 to 100 degrees relative to a longitudinal axis of the rotor.

10. The rotor of claim 9, wherein the first and second terminal impeller blade arrangements transition over the longitudinal axis of the rotor to define the central impeller blade arrangement.

11. A cavopulmonary assistance device, comprising:
an axial-centrifugal flow catheter pump comprising a rotor providing both an axial fluid flow and a centrifugal fluid flow and a motor operatively connected to the rotor;
a cable connected to the rotor and/or the motor; and
a deployable anchor for securing the cavopulmonary assistance device to a blood vessel wall;
the rotor including a first terminal impeller configured to provide a centrifugal and axial fluid flow in a first direction, a second terminal impeller configured to provide a centrifugal and axial fluid flow in a second direction opposite to the first direction, and a central impeller configured to provide a predominantly centrifugal fluid flow.

12. The cavopulmonary assistance device of claim 11, wherein the first and second terminal impellers each include blade arrangements configured to provide a centrifugal and axial fluid flow directed toward the rotor central impeller.

13. The cavopulmonary assistance device of claim 12, wherein the first and second terminal impeller blade arrangements include at least one blade oriented at an included angle of from 10 to 30 degrees relative to a longitudinal axis of the rotor.

14. The cavopulmonary assistance device of claim 11, wherein the central impeller includes a blade arrangement having at least one blade oriented at an included angle of from 80 to 100 degrees relative to a longitudinal axis of the rotor.

15. The cavopulmonary assistance device of claim 14, wherein the first and second terminal impeller blade arrangements transition over the longitudinal axis of the rotor to define the central impeller blade arrangement.

16. The cavopulmonary assistance device of claim 11, wherein the motor is directly connected to the rotor.

17. The cavopulmonary assistance device of claim 11, wherein the motor is remotely operatively connected to the rotor.

18. The cavopulmonary assistance device of claim 11, wherein the deployable anchor is configured to allow passage of fluid therethrough when deployed.

19. The cavopulmonary assistance device of claim 11, further including a bearing arrangement disposed at opposed ends of the rotor and a stator disposed at an end of the rotor opposed to the motor.

20. The cavopulmonary assistance device of claim 11, further including a protective enclosure surrounding at least the rotor, the protective enclosure being configured to allow fluid flow therethrough.

* * * * *